(12) United States Patent
Jerke

(10) Patent No.: US 9,358,060 B2
(45) Date of Patent: Jun. 7, 2016

(54) SELF-RETAINING DRIVER FOR A BONE SCREW

(71) Applicant: Zimmer Spine, Inc., Minneapolis, MN (US)

(72) Inventor: Eric P. Jerke, Bloomington, MN (US)

(73) Assignee: Zimmer Spine, Inc., Edina, MN (US)

( * ) Notice: Subject to any disclaimer, the term of this patent is extended or adjusted under 35 U.S.C. 154(b) by 333 days.

(21) Appl. No.: 13/950,419

(22) Filed: Jul. 25, 2013

(65) Prior Publication Data

US 2015/0032116 A1 Jan. 29, 2015

(51) Int. Cl.
*A61B 17/88* (2006.01)

(52) U.S. Cl.
CPC .......... *A61B 17/8875* (2013.01); *A61B 17/888* (2013.01); *A61B 17/8877* (2013.01); *A61B 17/8883* (2013.01); *A61B 17/8886* (2013.01); *A61B 17/8891* (2013.01)

(58) Field of Classification Search
CPC .......... A61B 17/7035; A61B 17/7037; A61B 17/8888; A61B 17/8886; A61B 17/8883; A61B 17/888; A61B 17/8875; A61B 17/8877; A61B 17/8891
See application file for complete search history.

(56) References Cited

U.S. PATENT DOCUMENTS

| | | | | |
|---|---|---|---|---|
| 2,474,994 | A * | 7/1949 | Tomalis | 411/404 |
| 3,888,144 | A * | 6/1975 | Parsons | 81/436 |
| 5,019,080 | A * | 5/1991 | Hemer | 606/104 |
| 5,435,680 | A * | 7/1995 | Schuster | 411/404 |
| 6,199,455 | B1 * | 3/2001 | Wagner | 81/121.1 |
| 6,299,616 | B1 * | 10/2001 | Beger | 606/86 R |
| 6,857,340 | B2 * | 2/2005 | Wagner | 81/121.1 |
| 6,921,402 | B2 | 7/2005 | Contiliano et al. | |
| 7,611,355 | B2 | 11/2009 | Murias | |
| 7,708,767 | B2 | 5/2010 | Contiliano et al. | |
| 8,016,836 | B2 | 9/2011 | Corrao et al. | |
| 8,291,795 | B2 * | 10/2012 | Hughes et al. | 81/460 |
| 8,394,108 | B2 | 3/2013 | McLean et al. | |
| 8,460,307 | B2 * | 6/2013 | Saidha et al. | 606/104 |
| 8,852,239 | B2 * | 10/2014 | Jackson et al. | 606/267 |
| 2001/0027320 | A1 | 10/2001 | Sasso | |
| 2002/0120275 | A1 | 8/2002 | Schmieding et al. | |
| 2003/0000351 | A1 | 1/2003 | Hawkes | |
| 2003/0032957 | A1 * | 2/2003 | McKinley | 606/61 |
| 2003/0093081 | A1 | 5/2003 | Hawkes | |
| 2003/0125749 | A1 | 7/2003 | Yuan et al. | |
| 2003/0149431 | A1 * | 8/2003 | Varieur | 606/61 |
| 2004/0122442 | A1 | 6/2004 | Lewis | |
| 2005/0038430 | A1 * | 2/2005 | McKinley | 606/61 |
| 2005/0085813 | A1 * | 4/2005 | Spitler et al. | 606/61 |
| 2005/0090899 | A1 * | 4/2005 | DiPoto | 623/17.11 |

(Continued)

*Primary Examiner* — Christian Sevilla
(74) *Attorney, Agent, or Firm* — Schwegman Lundberg & Woessner, P.A.

(57) ABSTRACT

A driver instrument for engaging and transferring rotational torque to a bone anchor already screwed into a bony structure. The driver instrument may be advanced through an incision while disengaged from the bone anchor and thereafter engaged in a driver socket of the bone anchor. The driver instrument includes an elongate shaft extending distally from a handle, a tapered distal tip, and a driver engagement feature located proximally of the tapered distal tip. The tapered distal tip and the driver engagement feature are configured such that the longitudinal rotational axis of the driver instrument automatically moves into parallel alignment with the longitudinal rotational axis of the bone anchor as the driver engagement feature of the driver instrument is advanced into the driver socket of the bone anchor.

18 Claims, 8 Drawing Sheets

(56) References Cited

U.S. PATENT DOCUMENTS

| | | | |
|---|---|---|---|
| 2006/0100622 A1* | 5/2006 | Jackson | 606/61 |
| 2006/0122604 A1* | 6/2006 | Gorhan et al. | 606/69 |
| 2006/0200131 A1* | 9/2006 | Chao et al. | 606/61 |
| 2007/0010821 A1 | 1/2007 | Wilkinson et al. | |
| 2007/0043379 A1* | 2/2007 | Sullivan et al. | 606/104 |
| 2008/0045970 A1* | 2/2008 | Saidha et al. | 606/104 |
| 2008/0234752 A1* | 9/2008 | Dahners | 606/291 |
| 2008/0319450 A1 | 12/2008 | Corrao et al. | |
| 2009/0042164 A1 | 2/2009 | Machata | |
| 2009/0131988 A1* | 5/2009 | Bush et al. | 606/280 |
| 2009/0163961 A1* | 6/2009 | Kirschman | 606/301 |
| 2009/0248029 A1 | 10/2009 | Paulos | |
| 2010/0228300 A1* | 9/2010 | Armstrong et al. | 606/301 |
| 2010/0248181 A1* | 9/2010 | Kremer et al. | 433/152 |
| 2010/0262196 A1* | 10/2010 | Barrus et al. | 606/308 |
| 2010/0298892 A1* | 11/2010 | Biyani et al. | 606/318 |
| 2011/0098715 A1* | 4/2011 | Laubert et al. | 606/104 |
| 2011/0245839 A1 | 10/2011 | Lower | |
| 2011/0245881 A1 | 10/2011 | Mitchell | |
| 2011/0270323 A1* | 11/2011 | Olsen et al. | 606/305 |
| 2011/0313471 A1* | 12/2011 | McLean et al. | 606/305 |
| 2012/0130388 A1 | 5/2012 | Plotkin | |
| 2013/0030476 A1* | 1/2013 | Shimko et al. | 606/308 |
| 2013/0213193 A1* | 8/2013 | Lukes | 81/436 |
| 2013/0261635 A1 | 10/2013 | Saidha et al. | |
| 2013/0268010 A1 | 10/2013 | Santangelo et al. | |
| 2014/0060268 A1* | 3/2014 | Goss | 81/460 |
| 2014/0066945 A1* | 3/2014 | Humphreys et al. | 606/104 |
| 2014/0277189 A1* | 9/2014 | Spratt et al. | 606/306 |

* cited by examiner

SELF-RETAINING DRIVER FOR A BONE SCREW

TECHNICAL FIELD

The disclosure is directed to a driver instrument for screwing a bone screw into a bony structure. More particularly, the disclosure is directed to a driver instrument configured to facilitate alignment and engagement with a bone screw as the driver instrument is advanced into the driver socket of the bone screw.

BACKGROUND

Bone anchors, such as bone screws, are commonly used in surgical procedures to attach constructs to a bony structure of a patient. For example, spinal stabilization constructs configured to stabilize a spinal segment may utilize bone screws to secure spinal rods or other elongate members to one or more vertebrae of a spinal column. The bone anchors may be screwed into the bony structure with a driver instrument.

However, in some instances it may be desirable to further screw the bone anchor into the bony structure and/or unscrew the bone anchor from the bony structure once the driver instrument has been disengaged from the bone anchor. Re-engaging the driver instrument with the bone anchor may be challenging. Accordingly, it is desirable to provide alternative driver instruments configured to engage with a bone anchor already installed in a bony structure.

SUMMARY

The disclosure is directed to several alternative designs, materials and methods of manufacturing medical device structures and assemblies, and uses thereof.

Accordingly, one illustrative embodiment is a method of installing a bone anchor into a bony structure. The method includes rotationally advancing a bone anchor into a bony structure to screw the bone anchor into the bony structure a first amount with a first driver instrument. The first driver instrument may then be disengaged from the bone anchor once the bone anchor has been screwed into the bony structure the first amount. Thereafter, a second driver instrument is advanced toward the bone anchor screwed into the bony structure after disengaging the first driver instrument from the bone anchor. A distal tip of the second driver instrument is advanced into a driver socket of the bone anchor screwed into the bony structure the first amount and a driver engagement feature of the second driver instrument is engaged with the driver socket of the bone anchor. The bone anchor is then further rotated (e.g., advanced and/or reversed) relative to the bony structure a second amount with the second driver instrument.

Another illustrative embodiment is a method of installing a bone anchor into a bony structure. The method includes screwing a threaded bone screw of a bone anchor into a bony structure a first amount with a first driver instrument. The bone anchor includes a housing pivotably coupled to a head of the threaded bone screw. The first driver instrument is then disengaged from a driver socket of the head of the bone screw once the bone screw has been screwed into the bony structure the first amount. Thereafter, a second driver instrument is advanced toward the bone screw screwed into the bony structure after disengaging the first driver instrument from the driver socket of the bone screw. The second driver instrument includes an elongate shaft extending distally from a handle, a tapered distal tip at a distal end of the elongate shaft, and a driver engagement feature located proximally of the tapered distal tip. The tapered distal tip of the second driver instrument is advanced into the driver socket of the bone screw screwed into the bony structure the first amount and the driver engagement feature of the second driver instrument is engaged with the driver socket of the bone screw as the tapered distal tip of the second driver instrument is further advanced into the driver socket of the bone screw. A longitudinal rotational axis of the second driver instrument moves into co-axial alignment with a longitudinal rotational axis of the bone screw as the driver engagement feature of the second driver instrument is engaged with the driver socket of the bone screw. The threaded bone screw of the bone anchor is then further screwed into the bony structure a second amount with the second driver instrument.

Yet another embodiment is a method of engaging a driver instrument with a bone anchor already screwed into a bony structure. The method includes advancing a driver instrument through an incision toward a bone anchor already screwed into the bony structure from a location exterior of the incision. The driver instrument is advanced through the incision while disengaged from the bone anchor. The driver instrument includes an elongate shaft extending distally from a handle, a tapered distal tip at a distal end of the elongate shaft, and a driver engagement feature located proximally of the tapered distal tip. The tapered distal tip of the driver instrument is advanced into a driver socket of the bone anchor after advancing the driver instrument through the incision and the driver engagement feature of the driver instrument is engaged with the driver socket of the bone anchor as the tapered distal tip of the driver instrument is further advanced into the driver socket of the bone anchor. The bone anchor is then rotated relative to the bony structure with the driver instrument.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 1:
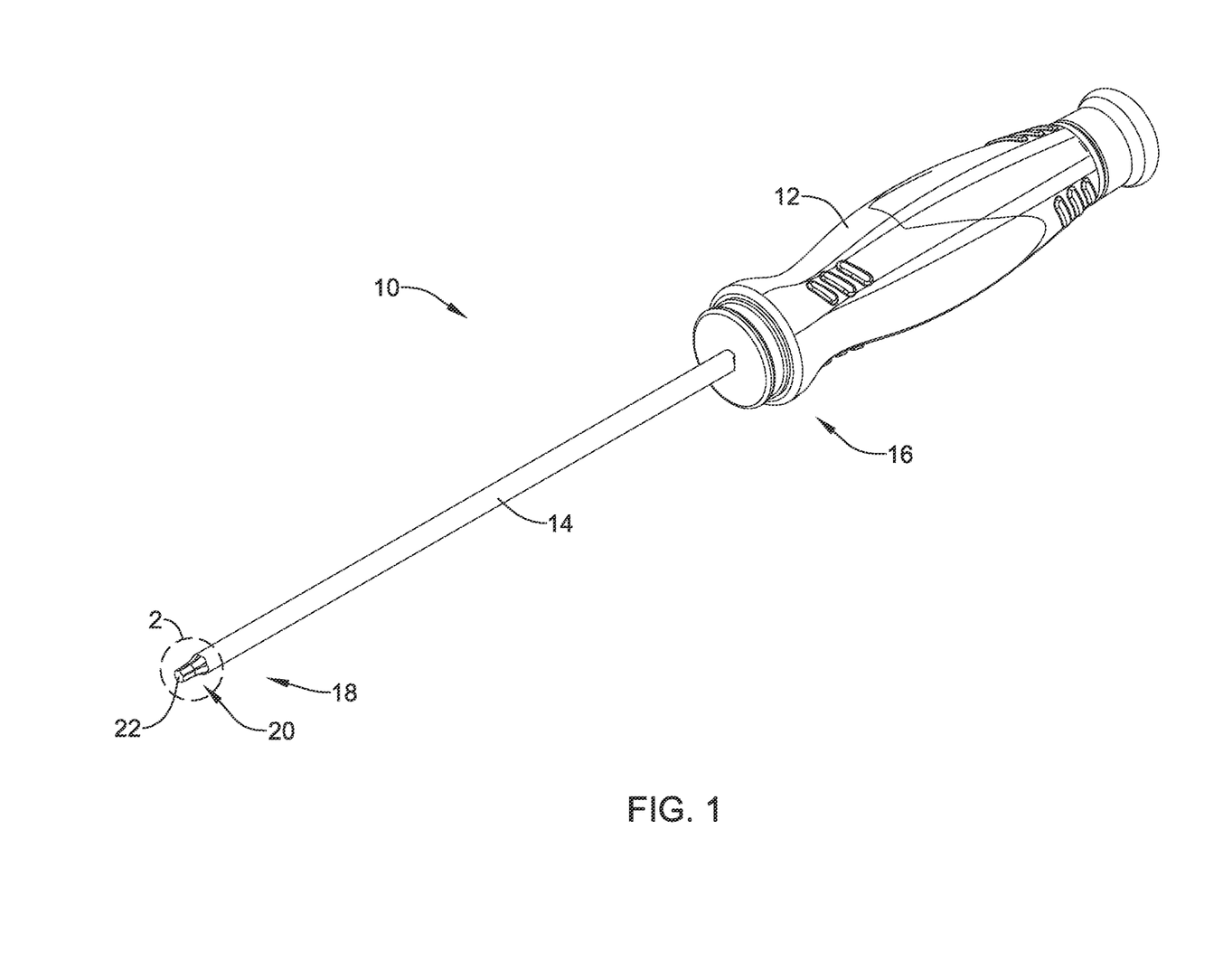
FIG. 1 is a perspective view of an exemplary instrument for rotationally driving a bone screw.

An exemplary driver instrument 10 is illustrated at FIG. 1. The driver instrument 10 includes a handle 12 and an elongate shaft 14 extending distally from the handle 12. In some instances, the handle 12 may be removably coupled to a proximal end 16 of the elongate shaft 14, such as with a quick connect feature. In other instances, the handle 12 may be permanently coupled to the proximal end 16 of the elongate shaft 14.

Figure 2:
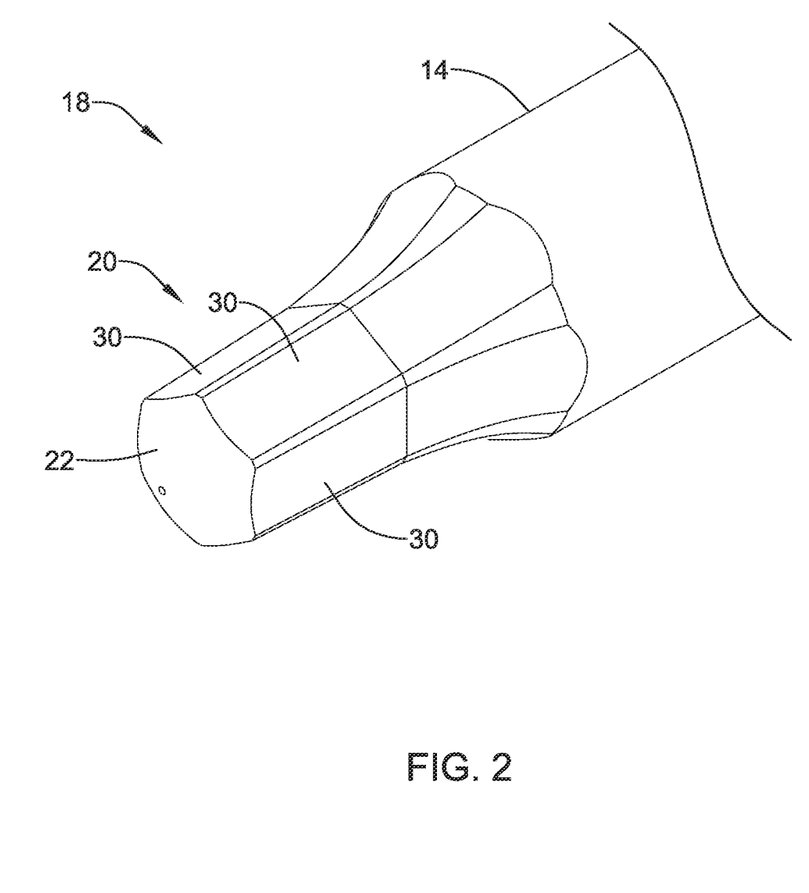
FIG. 2 is an enlarged perspective view of the distal end region of the driver instrument of FIG. 1.
Figure 3:
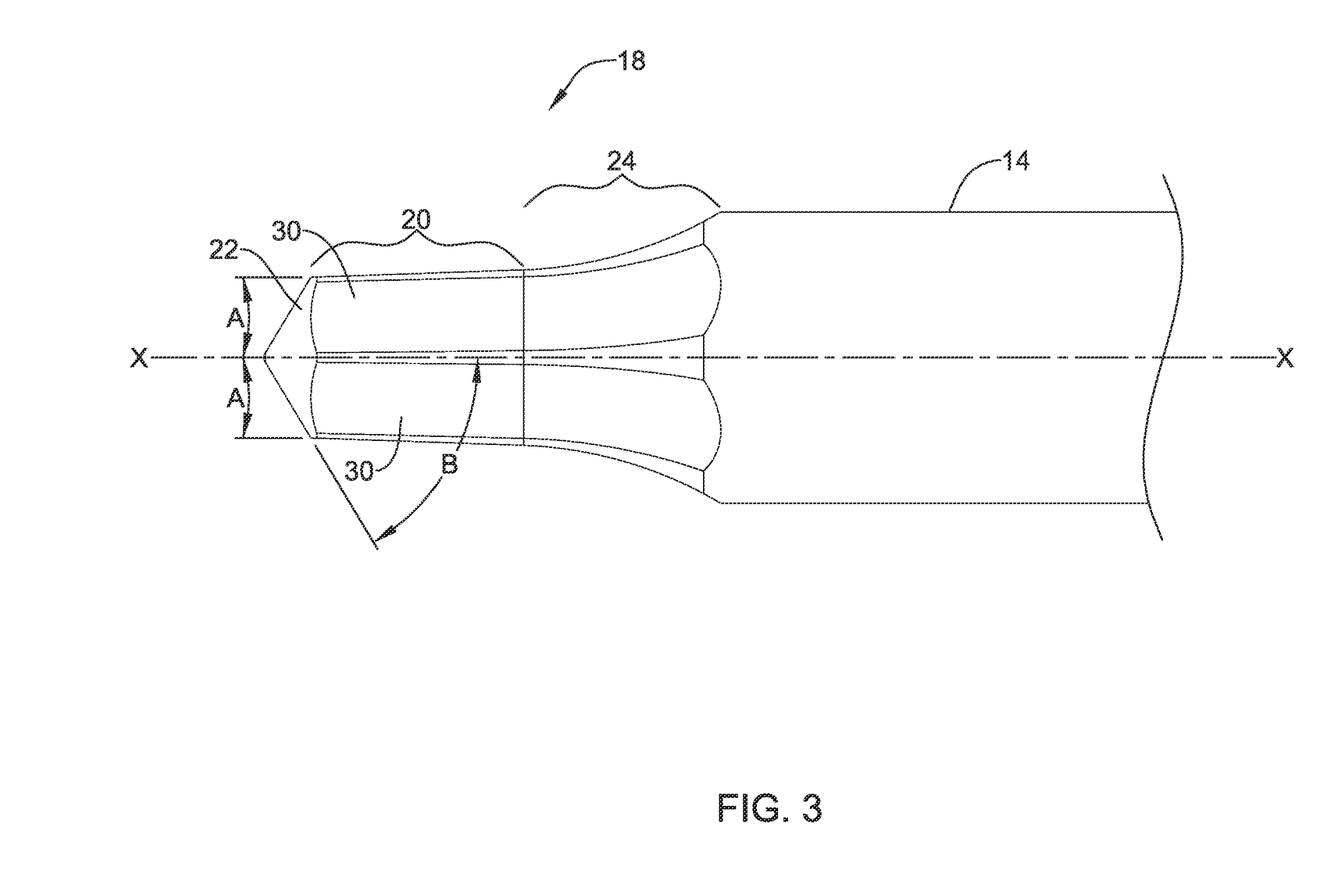
FIG. 3 is a side view of the distal end region of the driver instrument of FIG. 1.

The elongate shaft 14 may extend from the handle 12 to a distal end 18 of the elongate shaft 14. Aspects of the distal end 18 of the elongate shaft 14 are further illustrated at FIG. 2. The distal end 18 of the elongate shaft 14 may include a driver engagement feature 20 and a distal tip 22 extending distally of the driver engagement feature 20 to a distal extremity of the elongate shaft 14. As shown in FIG. 3, the elongate shaft 14 may include a transition region 24 proximal of the driver engagement feature 20 creating a transition from the driver engagement feature 20 to the main body portion of the elongate shaft 14 extending to the handle 12.

Figure 4:
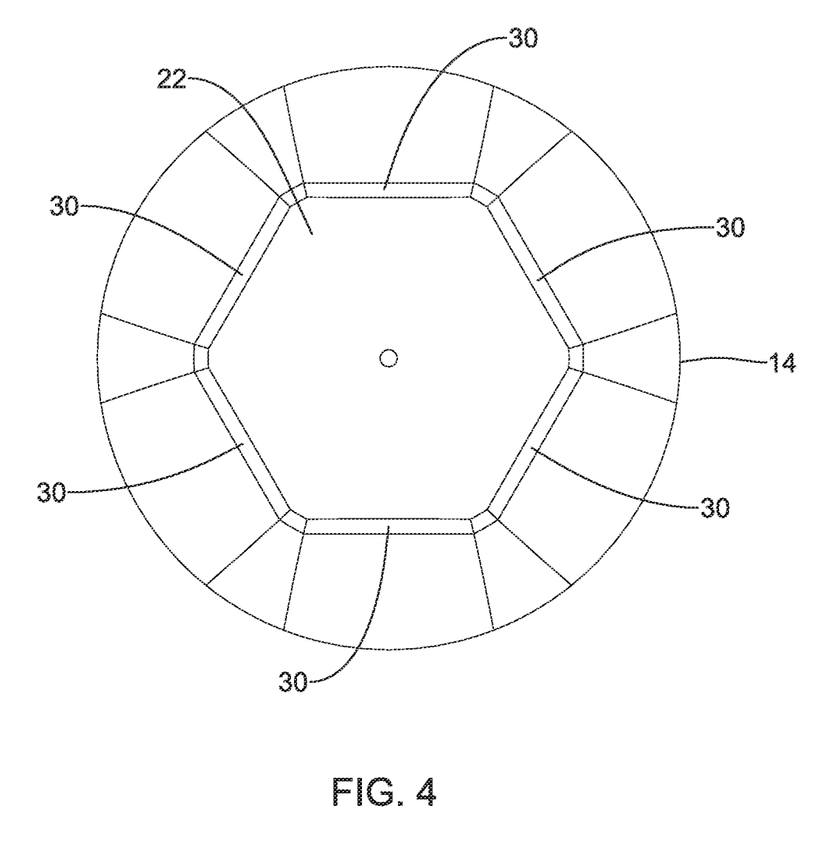
FIG. 4 is an end view of the distal end region of the driver instrument of FIG. 1.

The driver engagement feature 20 may be of any desired configuration for mating with a complementary driver engagement feature (e.g., a driver socket) of a bone screw. For example, the driver engagement feature 20 may be an internal driver configured to be inserted in and mate with a driver socket of a bone screw. For example, the driver engagement feature 20 may include a plurality of engagement surfaces 30 configured to engage a plurality of mating surfaces of the driver socket of a bone screw. In some instances the driver engagement feature 20 may be a hex driver, such as a hexalobular internal driving feature having six engagement surfaces 30 configured to engage six engagement surfaces of the driver socket of a bone screw. FIG. 4 is an end view of the driver instrument 10 showing six engagement surfaces 30 of the driver engagement feature 20 uniformly arranged in a polygonal configuration centered on the longitudinal rotational axis of the elongate shaft 14 of the driver instrument 10.

It is noted that other driver engagement structures, such as Torx®, may be utilized, if desired.

Referring to FIG. 3, in some instances each of the plurality of engagement surfaces 30 of the driver engagement feature 20 may be arranged nonparallel to the longitudinal rotational axis X of the driver instrument 10. For example, each of the plurality of engagement surfaces 30 may be positioned at an angle A from the longitudinal rotational axis X. In some instances, the angle A may be in the range of about 2 to about 8 degrees, about 2 to about 6 degrees, or about 4 to about 6 degrees from the longitudinal axis X, such as about 2 degrees, about 3 degrees, about 4 degrees, about 5 degrees, about 6 degrees, about 7 degrees, or about 8 degrees from the longitudinal rotational axis X. The tapered engagement surfaces 30 of the driver engagement feature 20 may facilitate advancing the driver engagement feature 20 into a mating driver socket, for example.

Furthermore, the distal tip 22 may be a tapered distal tip extending from the driver engagement feature 20 to the distal extremity of the driver instrument 10. In some instances, the tapered distal tip 22 may be tapered at an angle B from the longitudinal rotational axis X. In some instances, the angle B may be in the range of about 25 degrees to about 75 degrees, about 30 degrees to about 60 degrees, or about 45 degrees to about 60 degrees, such as about 30 degrees, about 45 degrees or about 60 degrees.

Accordingly, the second angle B of the tapered distal tip 22 may be greater than the first angle A between the engagement surfaces 30 and the longitudinal rotational axis X. Thus, the driver engagement feature 20 may be tapered toward the distal tip 22 a first amount, and the distal tip 22 may be tapered toward the distal extremity of the elongate shaft 14 a second amount greater than the first amount.

Figure 5:
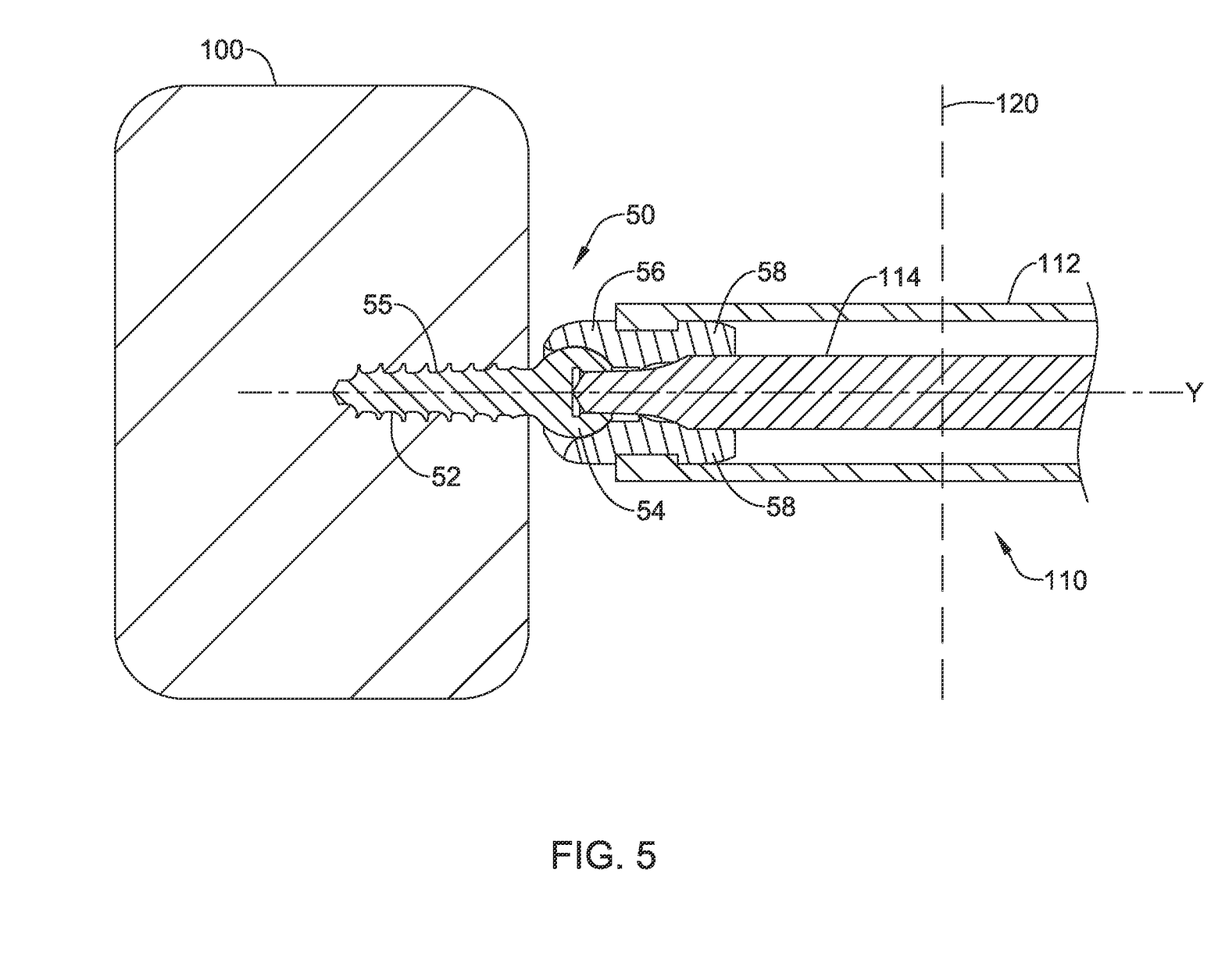
FIGS. 5-8 illustrate exemplary aspects of using the driver instrument of FIG. 1 for installing a bone screw.

FIGS. 5-8 illustrate exemplary aspects of using the driver instrument 10 of FIG. 1 for installing a bone anchor. As shown in FIG. 5, a bone anchor 50 may initially be installed in a bony structure 100 (e.g., a vertebra, sacrum, etc.) with a first driver instrument 110. The bone anchor 50 may include a threaded bone screw 52 having a head 54 and a threaded shank 55 extending distally from the head 54. The threaded shaft 55 may be configured to be screwed into the bony structure 100. The bone anchor 50 may also include a housing 56 coupled to the bone screw 52. The housing 56 may be configured to receive and retain an elongate stabilization member (e.g., a spinal rod, a flexible member, etc.) therein for constructing a stabilization system. For example, the housing 56 may include a pair of legs 58 defining a channel therebetween to receive an elongate stabilization member therebetween. A locking member, such as a set screw, may threadably engage a threaded opening between the legs 58 to retain the elongate stabilization member in the channel.

In some instances, the housing 56 may be movably coupled to the head 54 of the bone screw 52 such that the housing 56 be pivoted and/or rotated relative to the bone screw 52. For example, the bone anchor 50 may be a polyaxial screw in which the housing 56 may be pivoted and rotated in a plurality of orientations relative to the bone screw 52. For example, the bone screw 52 may have a longitudinal rotational axis Y (shown in FIG. 6) and the housing 56 may have a longitudinal axis Z (shown in FIG. 6), wherein the longitudinal axis Z of the housing 56 may be angled at a plurality of angles relative to the longitudinal rotational axis Y by pivoting the housing 56 about the head 54 of the bone screw 52. Furthermore, the housing 56 may be rotated relative to the head 54 of the bone screw 52 about the longitudinal axis Z.

The first driver instrument 110 may be any desired driver instrument adapted to rotationally advance the bone anchor 50 into the bony structure 100. For example, in some instances, the first driver instrument 110 may include a shaft 114 configured to engage a driver socket of the bone screw 52 with the longitudinal rotational axis of the shaft 114 coaxially aligned with the longitudinal rotational axis of the bone screw 52. The first driver instrument 110 may also include a sleeve 112 or other structure configured to engage the housing 56 to maintain the longitudinal axis of the housing 56 in coaxial alignment with the longitudinal rotational axis of the bone screw 52 as the first driver instrument 110 screws the bone screw 52 of the bone anchor 50 into the bony structure 100 a first amount. In some instances, the sleeve 112 may be positioned external to the housing 56. In other instances, the sleeve 112 may be positioned within the housing 56, such as within the threaded bore of the housing 56, or otherwise arranged in engagement with the housing 56. Accordingly, the first driver instrument 110 may be engaged with the bone anchor 50 to transfer rotational torque to the bone anchor 50 in order to screw the threaded bone screw 52 into the bony structure 100.

The bone anchor 50 may be rotationally advanced into the bony structure 100 to screw the bone anchor 50 into the bony structure 100 a first amount with the first driver instrument 110. Thereafter, the first driver instrument 110 may be disengaged from the bone anchor 50 (e.g., disengaged from a driver socket of the bone screw 52) once the bone anchor 50 has been screwed into the bony structure 100 the first amount.

In other embodiments, the driver instrument 10 may be used to pick up a bone anchor 50 from a surgical kit on a table of the operating room (or other location in the operating room) during a surgical procedure and transfer the bone anchor 50 from exterior of a patient, through an incision 120, to the bony structure 100, such that the driver instrument 10 is used to screw the bone anchor 50 into the bony structure 100 the first amount. Accordingly, in some instances the driver instrument 10 may be the only driver instrument used to advance the bone anchor 50 through the incision 120 and screw the bone anchor 50 into the bony structure 100.

Figure 6:
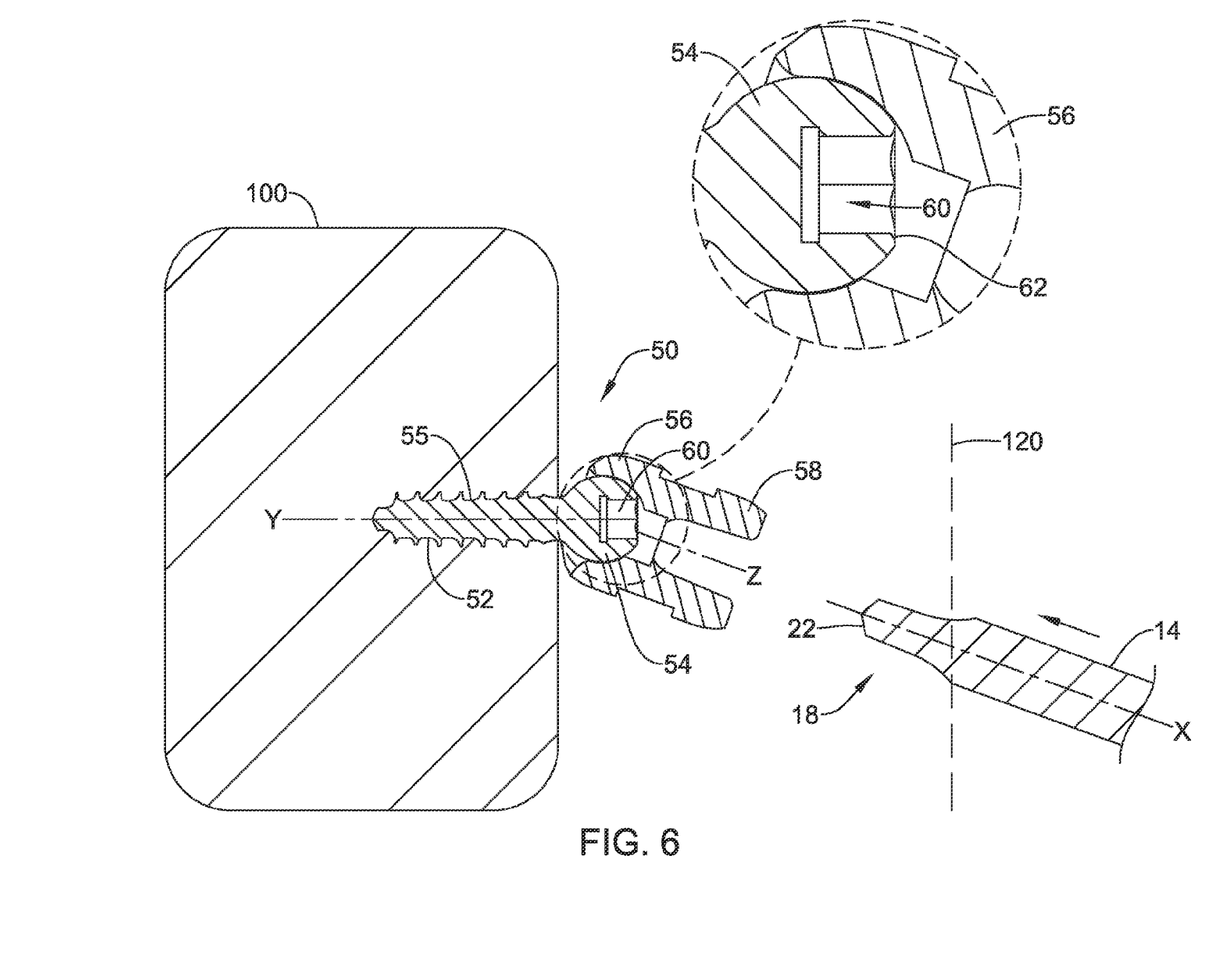

Turning to FIG. 6, if it is desired to further rotate the bone screw 52 of the bone anchor 50 relative to the bony structure 100 (e.g., advance or screw the bone anchor 50 into the bony structure 100 and/or reverse or unscrew the bone anchor 50 out of the bony structure 100), the second driver instrument 10 may be advanced toward the bone anchor 50 screwed into the bony structure 100 after disengaging the first driver instrument 110 from the bone anchor 50. It is noted that the first driver instrument 110 may be used to screw the bone anchor 50 into the bony structure 100 the first amount during a surgical procedure, and the second driver instrument 10 may be used to further screw the bone anchor 50 into the bony structure 100 (or otherwise rotate the bone screw 52 relative to the bony structure 100) a second amount during the same surgical procedure, or a subsequent surgical procedure. It is also contemplated that the driver instrument 10 may be used to initially screw the bone anchor 50 into the bony structure 100, thus removing the need for the first driver instrument 110.

As shown in FIG. 6, with the bone anchor 50 already screwed into the bony structure 100, the distal end 18 of the driver instrument 110 may be advanced through an incision 120 of the patient from a location exterior of the incision 120 while disengaged from the bone anchor 50. The distal end 18 of the driver instrument 10 may be advanced distally toward the head 54 of the bone screw 52. In some instances, the longitudinal rotational axis X of the driver instrument 10 may be nonparallel, and thus non-coaxial, to the longitudinal rotational 1 axis Y of the bone screw 52 as the distal end 18 of the shaft 14 of the driver instrument 10 is advanced toward the head 54 of the bone screw 52. In some instances, the longitudinal axis Z of the housing 56 may be nonparallel, and thus non-coaxial, to the longitudinal rotational axis Y of the bone screw 52 as the distal end 18 of the shaft 14 of the driver instrument 10 is advanced toward the head 54 of the bone screw 52. In other instances, the longitudinal rotational axis X of the driver instrument 10 may be parallel, and thus coaxial, to the longitudinal rotational 1 axis Y of the bone screw 52 and/or the longitudinal rotational axis Z of the housing 56 as the distal end 18 of the shaft 14 of the driver instrument 10 is advanced toward the head 54 of the bone screw 52.

Figure 7:
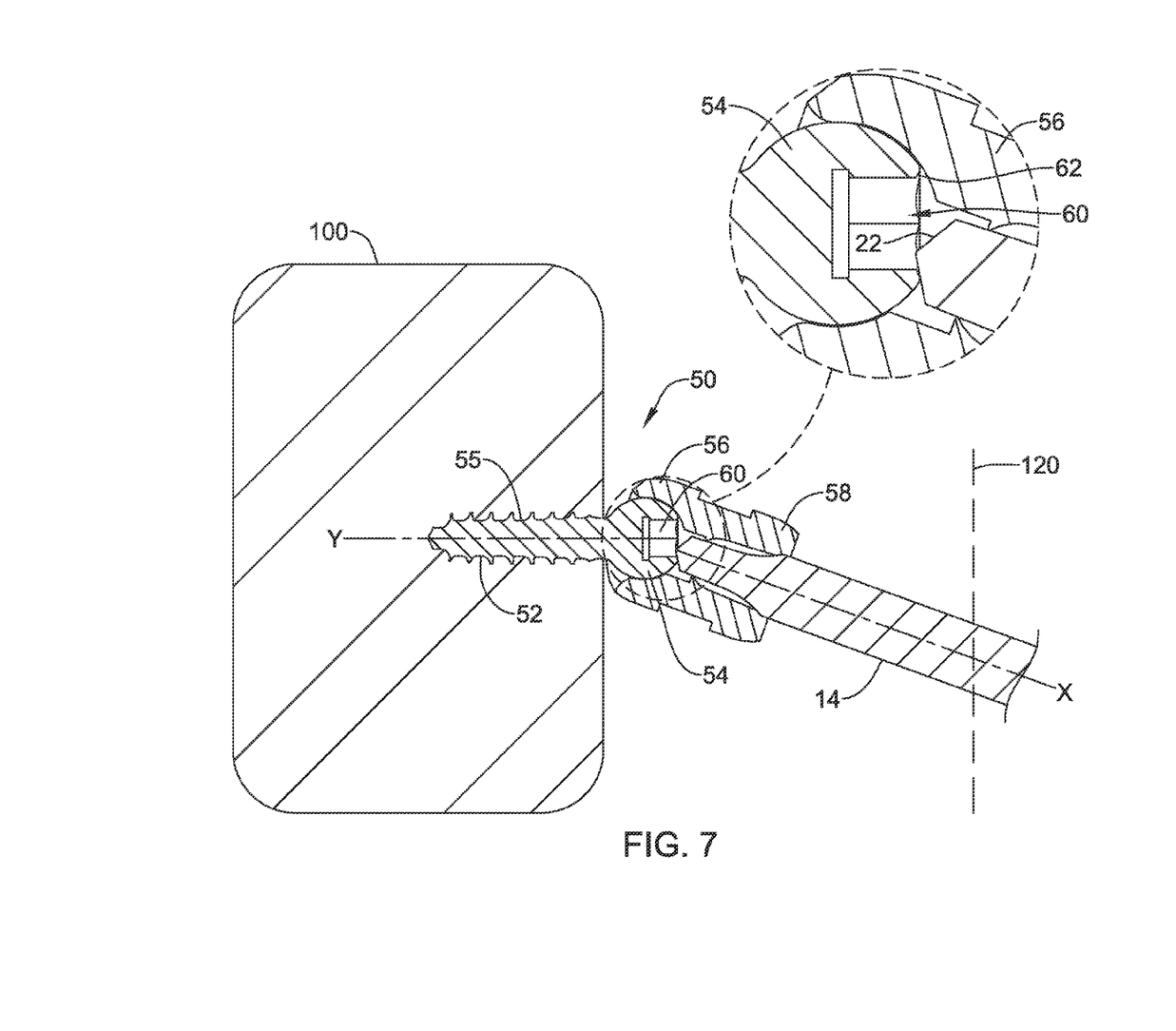

Turning to FIG. 7, as the driver instrument 10 is advanced distally, the distal tip 22 of the driver instrument 10 is advanced through the longitudinal bore of the housing 56 and into the driver socket 60 of the bone screw 52 screwed into the bony structure 100. The driver instrument 10 need not be coaxially aligned with the bone screw 52 as the distal tip 22 is advanced into the driver socket 60. The distal tip 22 may be tapered and/or the driver socket 60 may include a beveled rim 62 to facilitate advancement of the distal tip 22 into the driver socket 60.

In some instances, the longitudinal rotational axis X of the driver instrument 10 may be nonparallel, and thus non-coaxial, to the longitudinal rotational axis Y of the bone screw 52 as the distal tip 22 of the driver instrument 10 is advanced into the driver socket 60 of the head 54 of the bone screw 52. In some instances, the longitudinal axis Z of the housing 56 may be nonparallel, and thus non-coaxial, to the longitudinal rotational axis Y of the bone screw 52 as the distal tip 22 of the driver instrument 10 is advanced into the driver socket 60 of the head 54 of the bone screw 52. In other instances, the longitudinal rotational axis X of the driver instrument 10 may be parallel, and thus coaxial, to the longitudinal rotational axis Y of the bone screw 52 and/or the housing 56 as the distal tip 22 of the driver instrument 10 is advanced into the head 54 of the bone screw 52.

Figure 8:
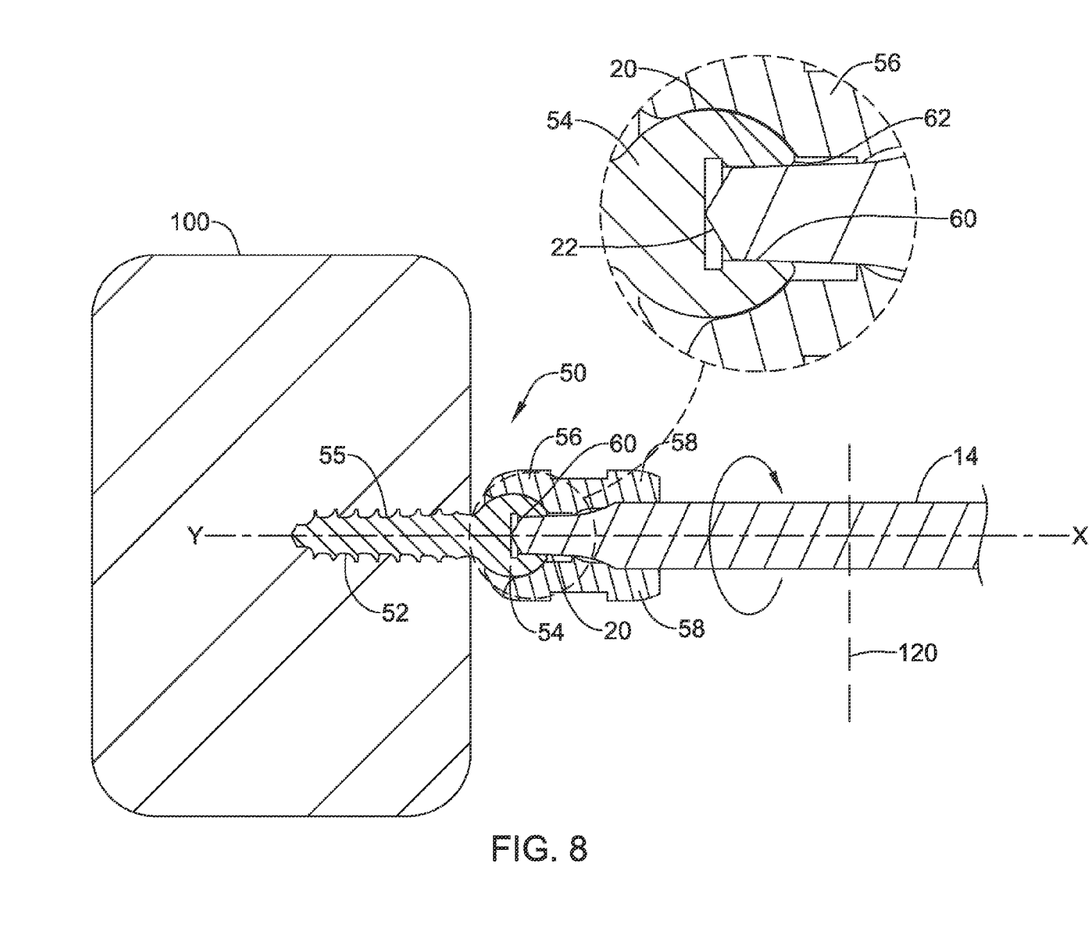

As the tapered distal tip 22 is further advanced into the driver socket 60 the driver engagement feature 20 of the driver instrument 10 may move into engagement with the driver socket 60 of the bone screw 52, as shown in FIG. 8. The configuration of the distal tip 22 and the driver engagement feature 20 may allow the longitudinal rotational axis X of the driver instrument 10 to automatically move into parallel, coaxial alignment with the longitudinal axis Y of the bone screw 52 as the driver engagement feature 20 of the driver instrument 10 is engaged with the driver socket 60 of the bone anchor 50. For example, the angled engagement surfaces 30 of the tapered driver engagement feature 20 may facilitate directing the driver engagement feature 20 into the driver socket 60 and mate the plurality of engagement surfaces 30 of the driver engagement feature 20 with a plurality of mating surfaces of the driver socket 60.

Once the driver engagement feature 20 is engaged in the driver socket 60 of the bone screw 52 the driver instrument 10 may be rotated to transfer rotational torque to the bone screw 52 and further rotate the bone screw 52 of the bone anchor 50 relative to the bony structure 100. For example, the driver instrument 10 may be rotated to further advance the bone screw 52 of the bone anchor 50 into the bony structure 100 a second amount to further tighten and/or orient the bone anchor 50 relative to the bony structure 100. In other instances, the driver instrument 10 may be rotated to reverse or unscrew the bone screw 52 of the bone anchor 50 from the bony structure 100 a second amount to remove and/or orient the bone anchor 50 relative to the bony structure 100.

Accordingly, the driver instrument 10 may facilitate engaging the head 54 of the bone screw 52 to further screw the bone screw 52 into the bony structure 100 a second amount after a first driver instrument 110 has been disengaged from the bone screw 52 after screwing the bone screw 52 into the bony structure 100 a first amount. In some instances, the bone screw 52 may be screwed into the bony structure 100 the first amount and the second amount during a single surgical procedure. In other instances, the bone screw 52 may be screwed into the bony structure 100 the first amount during a first surgical procedure and the bone screw 52 may be screwed into the bony structure 100 the second amount during a second surgical procedure, such as a revision procedure. In some instances, the driver instrument 10 may be used to unscrew the bone screw 52 from the bony structure 100, if desired.

It is noted that in instances in which the driver instrument 10 is engaged to the head 54 of the bone screw 52 exterior of the patient, (e.g., when the driver instrument is used to pick up a bone anchor 50 from a surgical kit on a table of the operating room (or other location in the operating room) during a surgical procedure and transfer the bone anchor 50 from exterior of a patient), similar steps as that described above may be employed. For example, the distal end 18 of the driver instrument 10 may be advanced distally toward the head 54 of the bone screw 52. In some instances, the longitudinal rotational axis X of the driver instrument 10 may be nonparallel, and thus non-coaxial, to the longitudinal rotational 1 axis Y of the bone screw 52 as the distal end 18 of the shaft 14 of the driver instrument 10 is advanced toward the head 54 of the bone screw 52. In some instances, the longitudinal axis Z of the housing 56 may be nonparallel, and thus non-coaxial, to the longitudinal rotational axis Y of the bone screw 52 as the distal end 18 of the shaft 14 of the driver instrument 10 is advanced toward the head 54 of the bone screw 52. In other instances, the longitudinal rotational axis X of the driver instrument 10 may be parallel, and thus coaxial, to the longitudinal rotational 1 axis Y of the bone screw 52 and/or the longitudinal rotational axis Z of the housing 56 as the distal end 18 of the shaft 14 of the driver instrument 10 is advanced toward the head 54 of the bone screw 52.

As the driver instrument 10 is advanced toward the bone screw 52, the distal tip 22 of the driver instrument 10 may be advanced through the longitudinal bore of the housing 56 and into the driver socket 60 of the bone screw 52. The driver instrument 10 need not be coaxially aligned with the bone screw 52 as the distal tip 22 is advanced into the driver socket 60. The distal tip 22 may be tapered and/or the beveled rim 62 of the driver socket 60 may facilitate advancement of the distal tip 22 into the driver socket 60.

In some instances, the longitudinal rotational axis X of the driver instrument 10 may be nonparallel, and thus non-coaxial, to the longitudinal rotational axis Y of the bone screw 52 as the distal tip 22 of the driver instrument 10 is advanced into the driver socket 60 of the head 54 of the bone screw 52. In some instances, the longitudinal axis Z of the housing 56 may be nonparallel, and thus non-coaxial, to the longitudinal rotational axis Y of the bone screw 52 as the distal tip 22 of the driver instrument 10 is advanced into the driver socket 60 of the head 54 of the bone screw 52. In other instances, the longitudinal rotational axis X of the driver instrument 10 may be parallel, and thus coaxial, to the longitudinal rotational axis Y of the bone screw 52 and/or the housing 56 as the distal tip 22 of the driver instrument 10 is advanced into the head 54 of the bone screw 52.

As the tapered distal tip 22 is further advanced into the driver socket 60 the driver engagement feature 20 of the driver instrument 10 may move into engagement with the driver socket 60 of the bone screw 52. The configuration of the distal tip 22 and the driver engagement feature 20 may allow the longitudinal rotational axis X of the driver instrument 10 to automatically move into parallel, coaxial alignment with the longitudinal axis Y of the bone screw 52 as the driver engagement feature 20 of the driver instrument 10 is engaged with the driver socket 60 of the bone anchor 50. For example, the angled engagement surfaces 30 of the tapered driver engagement feature 20 may facilitate directing the driver engagement feature 20 into the driver socket 60 and mate the plurality of engagement surfaces 30 of the driver engagement feature 20 with a plurality of mating surfaces of the driver socket 60.

The driver instrument 10, with the bone anchor 50 engaged therewith, may then be advanced through an incision of a patient to screw the bone screw 52 into a bony structure during a medical procedure. The driver instrument 10 may be used to rotationally advance the bone anchor 50 into a bony structure 100 to screw the bone anchor into the bony structure a first amount. Thereafter, the driver instrument may be used to rotate the bone anchor 50 a second amount (e.g., further rotationally advance and/or rotationally reverse the bone screw 52) relative to the bony structure 100.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of installing a bone anchor into a bony structure, comprising:

rotationally advancing a bone anchor into a bony structure to screw the bone anchor into the bony structure a first amount with a first driver instrument, the bone anchor comprising:
 a bone screw having a longitudinal rotational axis; and
 a housing pivotally coupled to a head of the bone screw, the housing having a longitudinal rotational axis that can be rotated up to a first angle from the longitudinal rotational axis of the bone screw;
 wherein the bone screw is rotationally advanced by the first driver while the longitudinal rotational axis of the housing is aligned with the longitudinal rotational axis of the bone screw;

disengaging the first driver instrument from the bone anchor once the bone screw has been screwed into the bony structure the first amount;

advancing a second driver instrument toward the bone screw screwed into the bony structure after disengaging the first driver instrument from the bone anchor;
 wherein the second driver instrument is advanced through the housing along the longitudinal rotational axis of the housing while the longitudinal rotational axis of the housing is offset from the longitudinal rotational axis of the bone screw;

advancing a distal tip of the second driver instrument into a driver socket of the bone screw screwed into the bony structure the first amount while the longitudinal rotational axis of the housing is offset from the longitudinal rotational axis of the bone screw;
 wherein the distal tip of the second driver instrument is tapered at a second angle relative to a longitudinal rotational axis of the second driver instrument such that the distal tip is able to enter the driver socket even when the housing is displaced at the first angle;

engaging a driver engagement feature of the second driver instrument with the driver socket of the bone anchor; and rotating the bone anchor relative to the bony structure a second amount with the second driver instrument.

2. The method of claim 1, wherein the longitudinal rotational axis of the second driver instrument is nonparallel to the longitudinal rotational axis of the bone screw as the distal tip of the second driver instrument is advanced into the driver socket of the bone anchor.

3. The method of claim 2, wherein the longitudinal rotational axis of the second driver instrument moves into parallel alignment with the longitudinal rotational axis of the bone screw as the driver engagement feature of the second driver instrument is engaged with the driver socket of the bone anchor.

4. The method of claim 3, wherein the longitudinal rotational axis of the housing is nonparallel to the longitudinal rotational axis of the bone screw as the distal tip of the second driver instrument is advanced into the driver socket of the bone anchor.

5. The method of claim 1, wherein an opening into the driver socket includes a beveled rim to facilitate advancement of the distal tip into the driver socket.

6. The method of claim 3, wherein the driver engagement feature of the second driver instrument is a hexalobular internal driving feature having six engagement surfaces configured to engage six engagement surfaces of the driver socket;

wherein the engagement surfaces of the hexalobular internal driving feature are nonparallel to the longitudinal rotational axis of the second driver instrument.

7. The method of claim 1, wherein the driver engagement feature of the second driver instrument includes a plurality of engagement surfaces configured to engage a plurality of mating surfaces of the driver socket;

wherein the engagement surfaces of the driver engagement feature are nonparallel to the longitudinal rotational axis of the second driver instrument.

8. The method of claim 7, wherein the plurality of engagement surfaces of the driver engagement feature extend at a third angle from the longitudinal rotational axis of the second driver instrument and the distal tip is tapered at the second angle from the longitudinal rotational axis of the second driver instrument, the second angle being greater than the third angle.

9. A method of installing a bone anchor into a bony structure, comprising:

screwing a threaded bone screw of a bone anchor into a bony structure a first amount with a first driver instrument using a sleeve that engages the bone anchor to ensure axial alignment between the threaded bone screw and the first driver instrument, the bone anchor including a housing pivotably coupled to a head of the threaded bone screw;

disengaging the first driver instrument from a driver socket of the head of the bone screw once the bone screw has been screwed into the bony structure the first amount, wherein the housing becomes non-coaxially aligned with the driver socket after the first driver instrument is disengaged;

advancing a second driver instrument toward the bone screw screwed into the bony structure after disengaging the first driver instrument from the driver socket of the bone screw, the second driver instrument including an elongate shaft extending distally from a handle, a tapered distal tip at a distal end of the elongate shaft, and a driver engagement feature located proximally of the tapered distal tip;

advancing the tapered distal tip of the second driver instrument into the driver socket of the bone screw screwed into the bony structure the first amount, the tapered distal tip being angled to allow the second driver to engage the driver socket when the housing is non-coaxially aligned with the driver socket;

engaging the driver engagement feature of the second driver instrument with the driver socket of the bone screw as the tapered distal tip of the second driver instrument is further advanced into the driver socket of the bone screw;

wherein a longitudinal rotational axis of the second driver instrument moves into co-axial alignment with a longitudinal rotational axis of the bone screw as the driver engagement feature of the second driver instrument is engaged with the driver socket of the bone screw; and further screwing the threaded bone screw of the bone anchor into the bony structure a second amount with the second driver instrument.

10. The method of claim 9, wherein the housing of the bone anchor has a longitudinal axis aligned with the longitudinal axis of the bone screw as the threaded bone screw is screwed into the bony structure the first amount with the first driver instrument.

11. The method of claim 10, wherein the longitudinal axis of the housing of the bone anchor is nonparallel with the longitudinal axis of the bone screw as the tapered distal tip of the second driver instrument is advanced into the driver socket of the bone screw.

12. The method of claim 9, wherein the longitudinal rotational axis of the second driver instrument is nonparallel to the longitudinal rotational axis of the bone screw as the distal tip of the second driver instrument is advanced into the driver socket of the bone screw.

13. The method of claim 9, wherein the distal tip of the second driver instrument is tapered to facilitate advancement of the distal tip into the driver socket.

14. The method of claim 13, wherein an opening into the driver socket includes a beveled rim to facilitate advancement of the distal tip into the driver socket.

15. The method of claim 9, wherein the driver engagement feature of the second driver instrument includes a plurality of engagement surfaces configured to engage a plurality of mating surfaces of the driver socket;

wherein the engagement surfaces of the driver engagement feature are nonparallel to the longitudinal rotational axis of the second driver instrument.

16. A method of engaging a driver instrument with a bone anchor already screwed into a bony structure, comprising:

advancing a driver instrument through an incision toward a bone anchor already screwed into the bony structure from a location exterior of the incision, wherein the driver instrument is advanced through the incision while disengaged from the bone anchor, the driver instrument including:

an elongate shaft extending distally from a handle, a tapered distal tip at a distal end of the elongate shaft, and a driver engagement feature located proximally of the tapered distal tip, the driver engagement feature comprising a plurality of planar engagement surfaces disposed nonparallel to the longitudinal rotational axis of the second driver instrument;

advancing the tapered distal tip of the driver instrument into a driver socket of the bone anchor at a non-parallel angle after advancing the driver instrument through the incision, wherein the tapered distal tip guides the planar engagement surfaces into engagement with the driver socket;

engaging the driver engagement feature of the driver instrument with the driver socket of the bone anchor as the tapered distal tip of the driver instrument is further advanced into the driver socket of the bone anchor, wherein the planar engagement surfaces facilitate parallel alignment of the driver instrument and the bone anchor; and rotating the bone anchor relative to the bony structure with the driver instrument.

17. The method of claim 1, wherein the bone screw is rotationally advanced by the first driver using a sleeve that maintains the longitudinal axis of the housing aligned with the longitudinal axis of the bone screw.

18. The method of claim 1, wherein the second angle is less than the first angle.

* * * * *